United States Patent
Boatright

(10) Patent No.: US 10,788,426 B2
(45) Date of Patent: *Sep. 29, 2020

(54) DETECTION OF HYDROPEROXIDES USING CHEMICALLY-STIMULATED LUMINESCENCE FROM STRUCTURED COMPOUND SEMICONDUCTORS

(71) Applicant: University of Kentucky Research Foundation, Lexington, KY (US)

(72) Inventor: William L. Boatright, Lexington, KY (US)

(73) Assignee: UNIVERSITY OF KENTUCKY RESEARCH FOUNDATION, Lexington, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/551,202

(22) Filed: Aug. 26, 2019

(65) Prior Publication Data

US 2019/0376901 A1 Dec. 12, 2019

Related U.S. Application Data

(63) Continuation-in-part of application No. 16/007,511, filed on Jun. 13, 2018.

(60) Provisional application No. 62/520,678, filed on Jun. 16, 2017.

(51) Int. Cl.
| | |
|---|---|
| *G01N 21/64* | (2006.01) |
| *G01N 21/76* | (2006.01) |
| *G01N 33/02* | (2006.01) |
| *G01N 33/15* | (2006.01) |
| *G01N 33/28* | (2006.01) |
| *G01N 33/84* | (2006.01) |
| *G01N 31/22* | (2006.01) |
| *G01N 33/53* | (2006.01) |

(52) U.S. Cl.
CPC ......... *G01N 21/6489* (2013.01); *G01N 21/76* (2013.01); *G01N 31/228* (2013.01); *G01N 33/02* (2013.01); *G01N 33/15* (2013.01); *G01N 33/28* (2013.01); *G01N 33/5308* (2013.01); *G01N 33/84* (2013.01)

(58) Field of Classification Search
CPC .... G01N 21/6489; G01N 21/76; G01N 33/02; G01N 33/15; G01N 33/28; G01N 33/5308; G01N 33/84; G01N 33/20; G01N 31/22; G01N 31/228; Y10T 436/16; Y10T 436/20; Y10T 436/203332; Y10T 436/206664; B82Y 30/00
USPC ..... 436/20, 81, 84, 127, 131, 135, 164, 166, 436/103, 60
See application file for complete search history.

(56) References Cited

U.S. PATENT DOCUMENTS

| | | | | |
|---|---|---|---|---|
| 4,752,588 A | * | 6/1988 | Ellis | ..................... G01N 21/643 250/361 R |
| 2018/0217149 A1 | * | 8/2018 | Bouzigues | ........... G01N 33/582 |

OTHER PUBLICATIONS

Azizi et al. Journal of Spectroscopy, vol. 2013, article ID 803592, pp. 1-8, published in 2013.*

* cited by examiner

*Primary Examiner* — Maureen Wallenhorst
(74) *Attorney, Agent, or Firm* — King & Schickli, PLLC

(57) ABSTRACT

A method of monitoring for the presence of a hydroperoxide in an aqueous or non-polar environment includes steps of exposing a structured compound semiconductor material with peroxidase activity to the hydroperoxide in the environment and detecting electromagnetic radiation emitted by the structured compound semiconductor material with peroxidase activity upon exposure to the hydroperoxide. The luminescence emitting semiconductor material with peroxidase activity consists of a primary semiconductor material with a dopant prepared on a phytate scaffold.

18 Claims, 18 Drawing Sheets

US 10,788,426 B2

DETECTION OF HYDROPEROXIDES USING CHEMICALLY-STIMULATED LUMINESCENCE FROM STRUCTURED COMPOUND SEMICONDUCTORS

This application is a continuation-in-part of U.S. patent application Ser. No. 16/007,511 filed on Jun. 13, 2018, which claims the benefit of U.S. Patent Application Ser. No. 62/520,678 filed on Jun. 16, 2017, the full disclosure of which is incorporated herein by reference.

TECHNICAL FIELD

This document relates generally to the field of compound semiconductors and, more particularly, to compound semiconductors useful to detect and quantify the level of hydroperoxide in both aqueous and non-polar environments as well as to related methods.

BACKGROUND

"Reactive oxygen substances" or "ROS" means an active chemical species containing oxygen. Examples include hydroperoxides, peroxides, superoxide radical anion, hydroxyl radical and singlet oxygen. Free radicals are atoms or molecules with unpaired electrons. These radicals are highly reactive and can catalyze a variety of degradative reactions. Examples of free radical catalyzed reactions include enzymatic reactions associated with organelles, lipid autoxidation, the oxidation of macromolecules leading to damage at cellular and tissue levels, oxidation of cholesterol and the formation of arterial plaques and the development of arteriosclerosis, and the oxidation of Beta-amyloid proteins and the development of senile dementia or Alzheimer's disease. The breakdown of unsaturated hydrocarbons (e.g. fatty acids) into ketones, alcohols, and aldehydes is a multi-step free-radical process (often involving hydroperoxides) and depends on several cofactors, reaction conditions, and chemicals. Some ROS are free radicals (e.g., superoxide radical anion, hydroxyl radical) and some ROS such as hydroperoxides can rapidly breakdown to form free radicals. Other types of radicals and oxidative reactive substances include reactive nitrogen substances and carbon radicals. Carbon radicals can react rapidly with oxygen to form hydroperoxides. In the fields of medical, agricultural, petrochemical and pharmacological sciences there is a need for novel methods to detect hydroperoxides.

The general principle of luminescent emission from compound semiconductors is dependent on the sequence of events involving electrons traps and holes. In the case of photo-stimulated luminescence, energy inputs necessary for these conditions occur as a result of absorption of a photon in a designed nanoscale system. One major area of photo-stimulated luminescence from compound semiconductors, collectively referred to as Quantum dots (QDs), are colloidal nanocrystalline semiconductors possessing unique properties due to quantum confinement effects. Once stimulated by electromagnetic energy sources, the luminescence wavelengths emitted is strongly dependent on its composition, which often includes some form of dopant.

One such dopant is manganese. Examples include manganese-activated $ZnGa_2O_4$ prepared at a sintering temperature of 1,375° C. with 0.1% MnO dopant which emits red and green light with peaks at 666 and 508 nm when excited with a laser source (325 nm). In another example of photo-stimulated luminescence from compound semiconductors, two independent luminescence channels have been observed from manganese-doped spinel $Mn:MgAl_2O_4$. The luminescence around 520 nm is assigned to transition from the conduction hand of the excited state $^4T_1$ to the ground state $^6A_1$ at the valence hand of $Mn^{2+}+(3d)5$ ion by analyzing the excitation spectrum and electron spin resonance measurement.

Current techniques for detecting hydroperoxides include fluorescent or spectrophotometric techniques (e.g., the Amplex Red and Leucocrystal Violet techniques); however, both of these techniques require an extensive incubation time for the development of the reaction product that is ultimately detected. There are a number of commercially available kits that can measure hydroperoxides and that are based on chromogen formation from ferric iron-xylenol orange complex or ferric thiocyanate. These kits exhibit an array of different problems. In the field of chemical luminescence there exists luminescence enhancers like luminol, lucigenin and even the carbonate radical; however these all have severe limitations (e.g., requiring a strong alkaline pH and solubility restrictions).

Peroxide value (PV) is the most widely used analytical technique for measuring the degree of oxidation (as hydroperoxide content) in edible fats, oils and petrochemicals. This titration technique was first developed for non-food applications in the 1880s. The term "peroxide value" was used in publications from the 1920s based on the observations that the development of rancidity was associated with the uptake of oxygen by edible oils. Lea published an iodometric method for the determination of peroxides in edible fats and oils by heating fat with powdered potassium iodide in a mixture of chloroform-acetic acid. This mixture was then titrated with sodium thiosulfate solution to measure the liberated iodine. The next year, Wheeler presented modifications to this iodometric titration method. In 1949 PV, based on the techniques of Lea and Wheeler, was adopted as the official method by the AOCS, and with the exception of the replacement of chloroform with isooctane in the 1990s, it has remained essentially the same. Official methods for measuring PV in edible oil are established by the American Oil Chemists Society (AOCS) Official Method Cd 8b-90, International Union of Pure and Applied Chemistry (IUPAC) 2.501, International Organization for Standardization (ISO) 3960:2017 or U.S. Pharmacopeial Convention methods (USP) 401.

Data presented in this document is the first to demonstrate that luminescence emissions can be generated from structured compound semiconductors in real time as a result of chemical stimulation by ROS. Furthermore, these light emissions can be used to quantify the level of hydroperoxides. These compounds exhibit concentration-dependent chemically-stimulated luminescence when reacted with various types of ROS such as solutions of cumene-hydroperoxide, aqueous solution of hydrogen peroxide, oxidized edible oils and oxidized mineral oils.

SUMMARY

In accordance with the purposes and benefits described herein, a new and improved method is provided for monitoring for the presence of a hydroperoxides in an environment such as an aqueous environment or a non-polar environment. That method broadly includes the steps of: exposing a structured compound semiconductor material with peroxidase activity to the hydroperoxide in the environment and detecting electromagnetic radiation emitted by the structured compound semiconductor material with peroxidase activity upon exposure to the hydroperoxide.

The method may further include measuring the electromagnetic radiation emitted by the structured compound semiconductor material with peroxidase activity. Further, the method may include quantifying the hydroperoxide in the environment.

Still further, the method may include monitoring the presence of the hydroperoxide in an aqueous environment. Alternatively, the method may include monitoring the presence of the hydroperoxide in a non-polar environment.

Still further, the method may include monitoring the presence of the hydroperoxide in food, in pharmaceuticals, in biological materials or in petrochemical materials.

Still further, the method may include producing the structured compound semiconductor material with peroxidase activity from a phytate scaffold material and a metal dopant. The structured compound semiconductor with peroxidase activity emits electromagnetic radiation upon exposure to a hydroperoxide.

In accordance with an additional aspect, a structured compound semiconductor material with peroxidase activity is provided. That structured compound semiconductor material with peroxidase activity comprises a phytate scaffold material, a primary semiconducting material and a metal dopant wherein the structured compound semiconductor material with peroxidase activity emits electromagnetic radiation upon exposure to a hydroperoxide.

In at least one of the many possible embodiments of the structured compound semiconductor material with peroxidase activity, the primary semiconducting material is zinc and the metal dopant is manganese. That phytate may be present at from 3.0-50.0 mole percent, that zinc may be present at from 18.0-80.0 mole percent and that manganese may be present at from 0.1-10.0 mole percent. In one particularly useful embodiment, the manganese is present at 0.1-5.0 and more specifically about 0.5 mole percent.

In at least one of the many possible embodiments, the structured semiconductor material is derived from naturally occurring materials such as rice bran or the plasma ash from rice products (e.g., rice bran or rice protein concentrates). In at least one of the many possible embodiments, the structured semiconductor material is prepared using phytic acid or phytic acid chemically modified with ethanolamine.

In at least one embodiment of the method, the environment is an aqueous environment. In at least one embodiment of the method, the environment is a non-polar environment.

For purposes of this document, the terminology "free radicals" means atoms or molecules with unpaired electrons that are highly reactive and are capable of catalyzing a variety of degenerative reactions.

For purposes of this document, the terminology "reactive oxygen substances" or "ROS" means chemically active chemical species containing oxygen. Examples include hydroperoxides, peroxides, superoxide, hydroxyl radical and singlet oxygen.

For purposes of this document, the terminology "phytate scaffold material" refers to phytate and phytic acid derived materials capable of functioning as a scaffold for holding one or more semiconductors and functioning as a structured compound semiconductor material with peroxidase activity.

In the following description, there are shown and described several preferred embodiments of the method for monitoring for the presence of a hydroperoxide in an environment as well as to structured compound semiconductor materials with peroxidase activity useful in such a method. As it should be realized, the method and structured compound semiconductor materials with peroxidase activity are capable of other, different embodiments and their several details are capable of modification in various, obvious aspects all without departing from the method and materials as set forth and described in the following claims. Accordingly, the drawings and descriptions should be regarded as illustrative in nature and not as restrictive.

BRIEF DESCRIPTION OF THE DRAWING FIGURES

The accompanying drawing figures incorporated herein and forming a part of the specification, illustrate several aspects of the method and related materials and together with the description serve to explain certain principles thereof.

FIG. 1 illustrates luminescence over time emitted from rice protein concentrate ash hydrated with 22 mM hydrogen peroxide in 0.2 M phosphate buffer, pH 7.2. Ashing conditions were high-temperature at 580° C. and low-temperature plasma asking at 150° C. Luminescence range was 350-650 nm.

Figure 3:
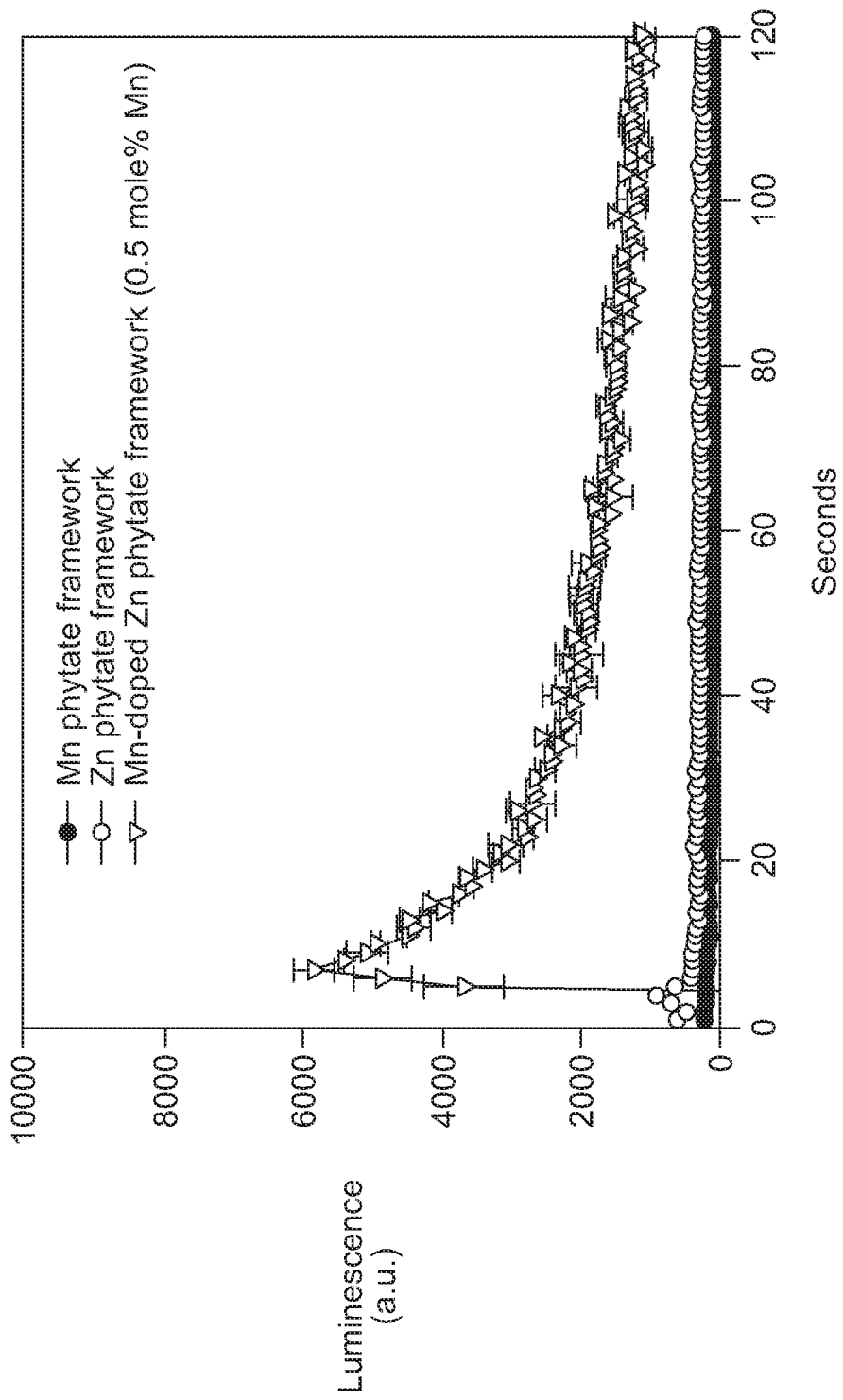

FIG. 3 illustrates luminescence emitted over time from zinc, manganese or zinc/manganese deposited on a phytic acid scaffold. All hydrated in 0.2 M phosphate buffer, pH 7.2 with either 22 mM hydrogen peroxide, (n=3). Luminescence range was 350-650 nm.

Figure 4:
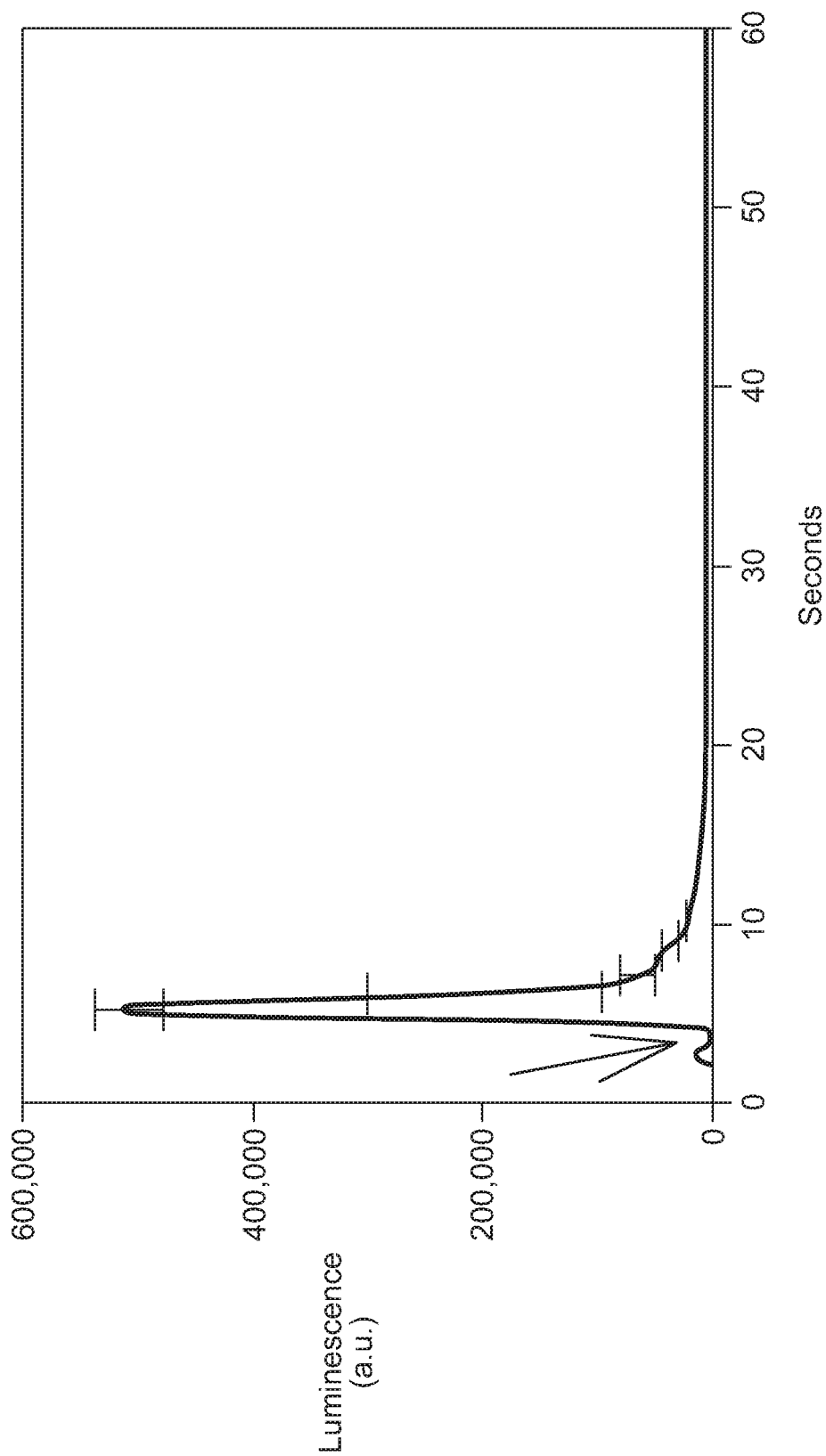

FIG. 4 illustrates chemically-stimulated luminescence emitted from 0.5 mole % Mn-doped Zn phytate ethanolamine hydrated with 1.5 mL 25 mM of hydrogen peroxide. The arrow denotes moment of solvent addition to the powder material. Luminescence from 350-650 nm minus the blank without $H_2O_2$. (n=2)

Figure 5:
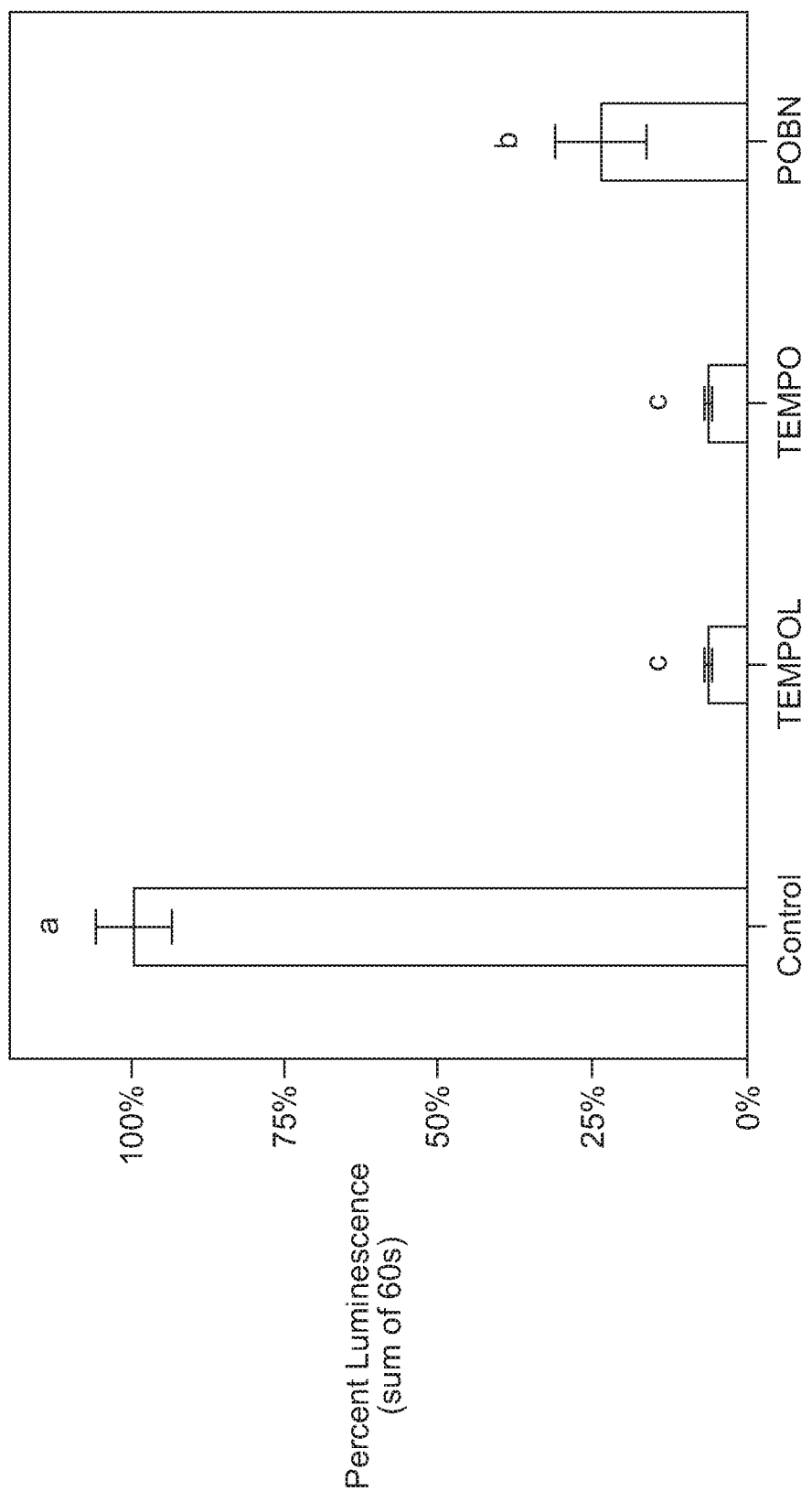

FIG. 5 illustrates the effect on chemically-stimulated luminescence from zinc/manganese structured compound semiconductor hydrated with solutions containing different water soluble radical quenchers including TEMPOL, TEMPO or POBN (25 mM) and hydrogen peroxide (25 mM). (n=3). Different letters indicate difference at 95% confidence level.

Figure 6:
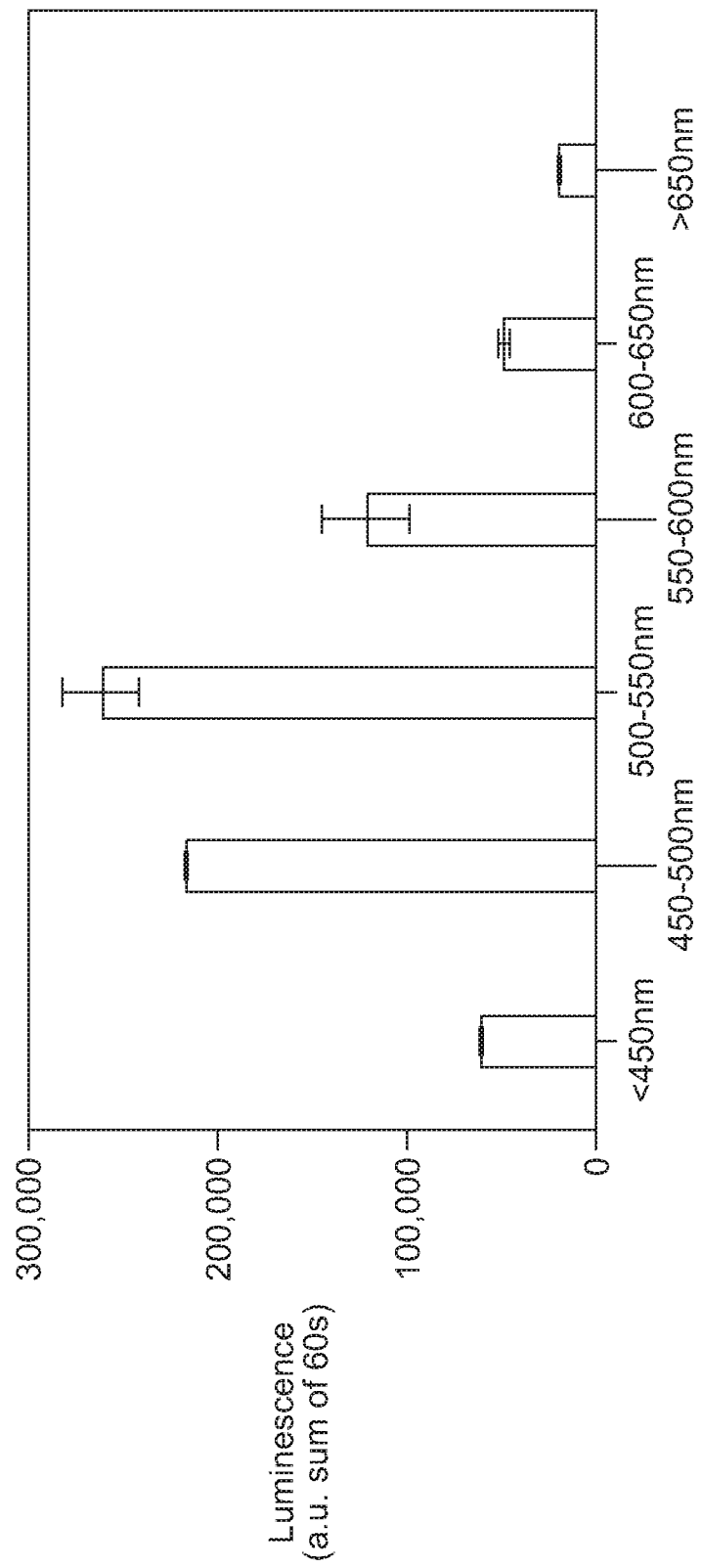

FIG. 6 illustrates wavelength range distribution of the chemically-stimulated luminescence from zinc/manganese structured compound semiconductor hydrated with 25 mM hydrogen peroxide. (n=2).

Figure 7:
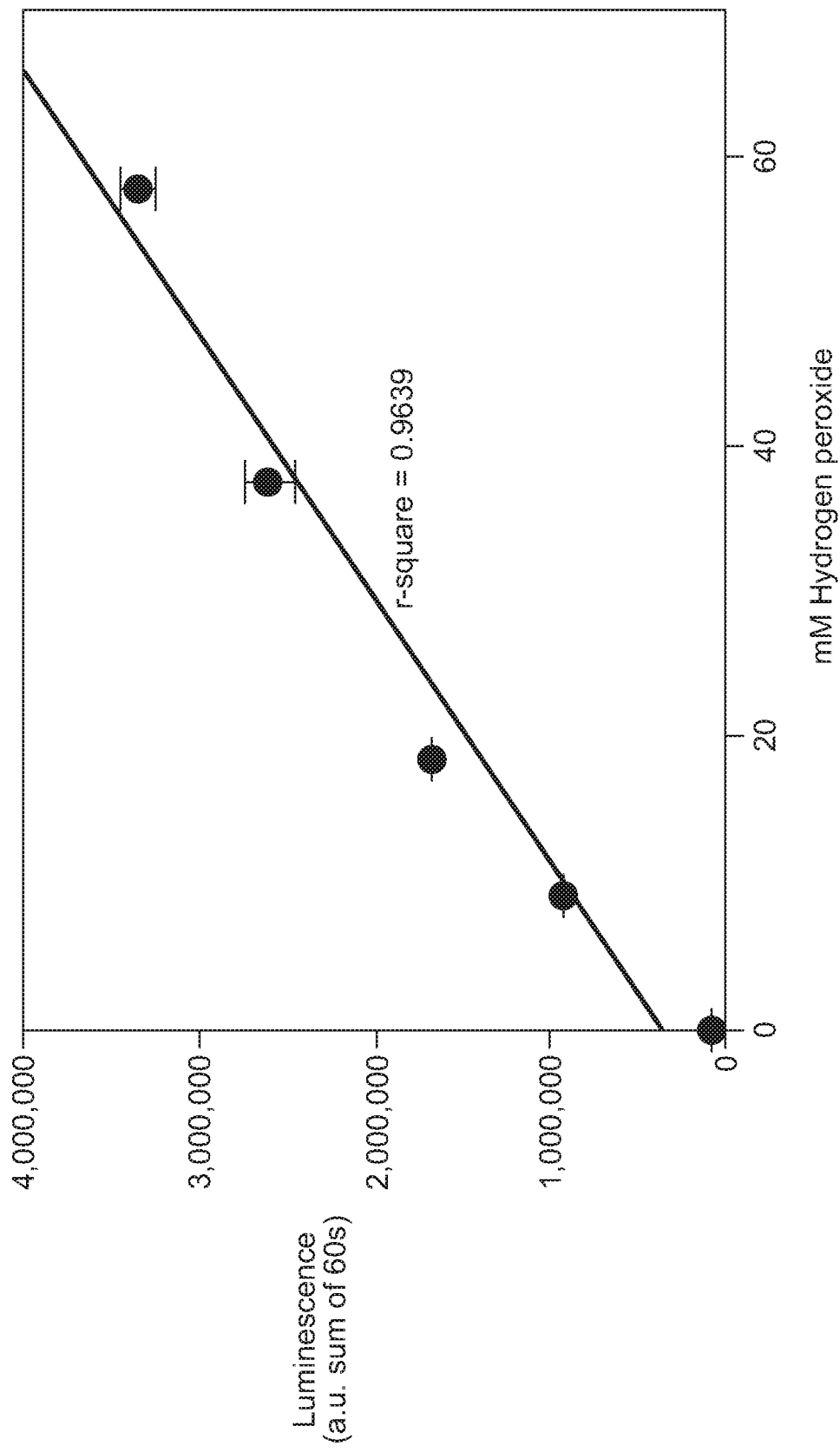

FIG. 7 illustrates the novel structured semiconductors material at 0.5 mole % of manganese doping exhibited strong linearity (r-squared greater than 0.95) between chemically stimulated luminescence and hydrogen peroxide level.

Figure 8:
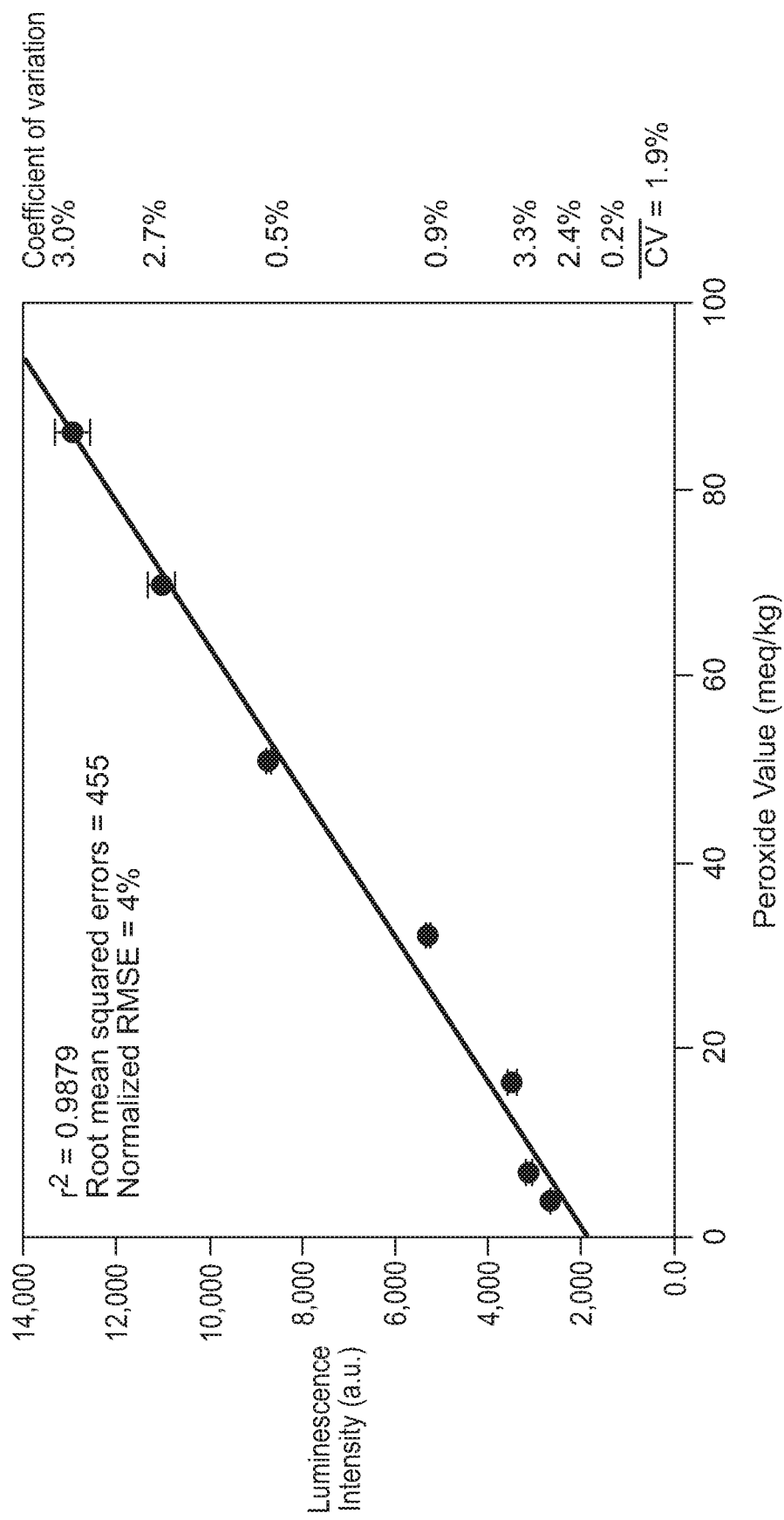

FIG. 8 illustrates luminescences intensity from 25 ng $MnZn_4$/phytic acid in 2.5 mLs soybean oil. Luminescence range was 350-650 nm.

Figure 9:
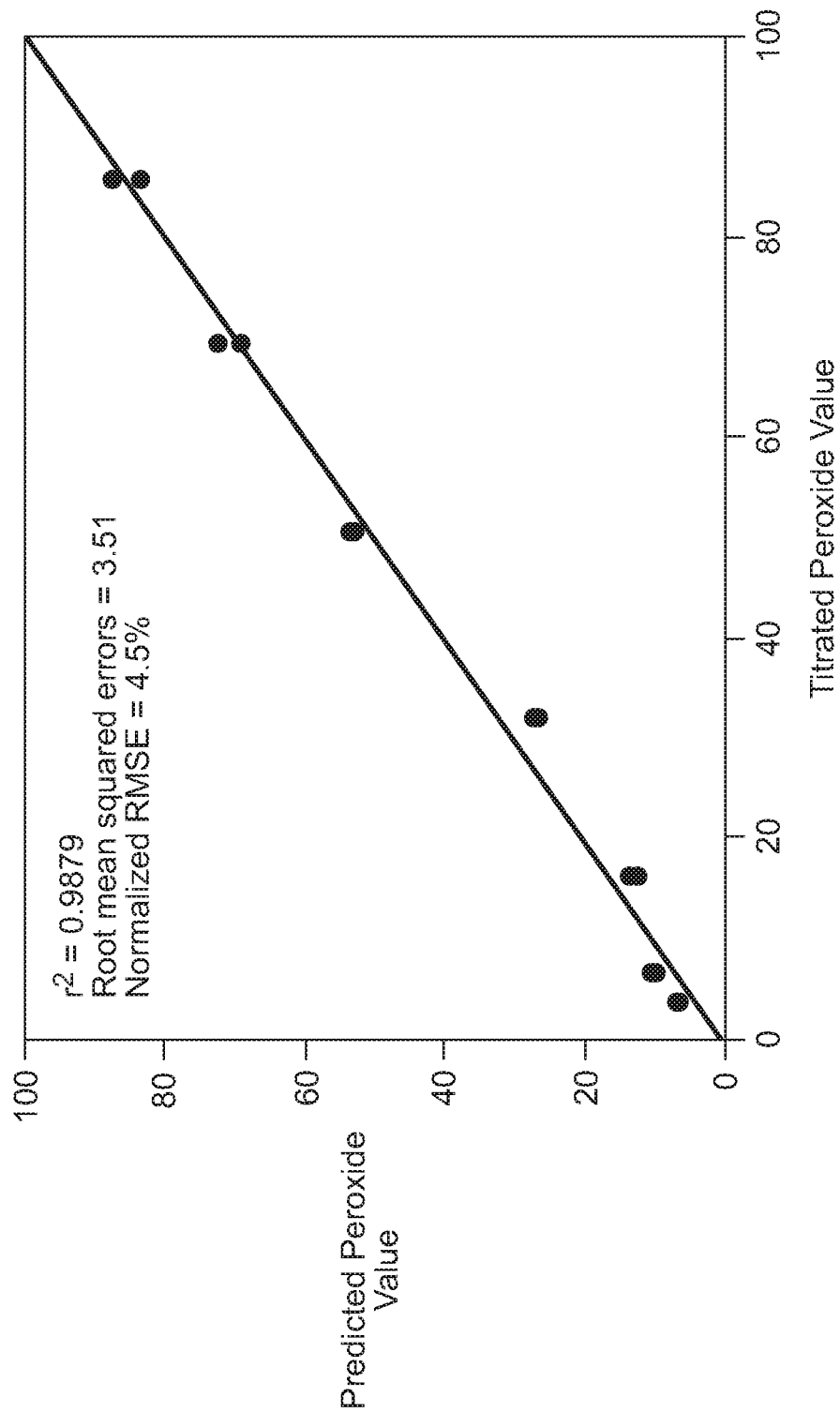

FIG. 9 illustrates titrated PV vs. predicted PV from luminescence (meq/kg from refined, bleached and deodorized soybean oil).

Figure 10:
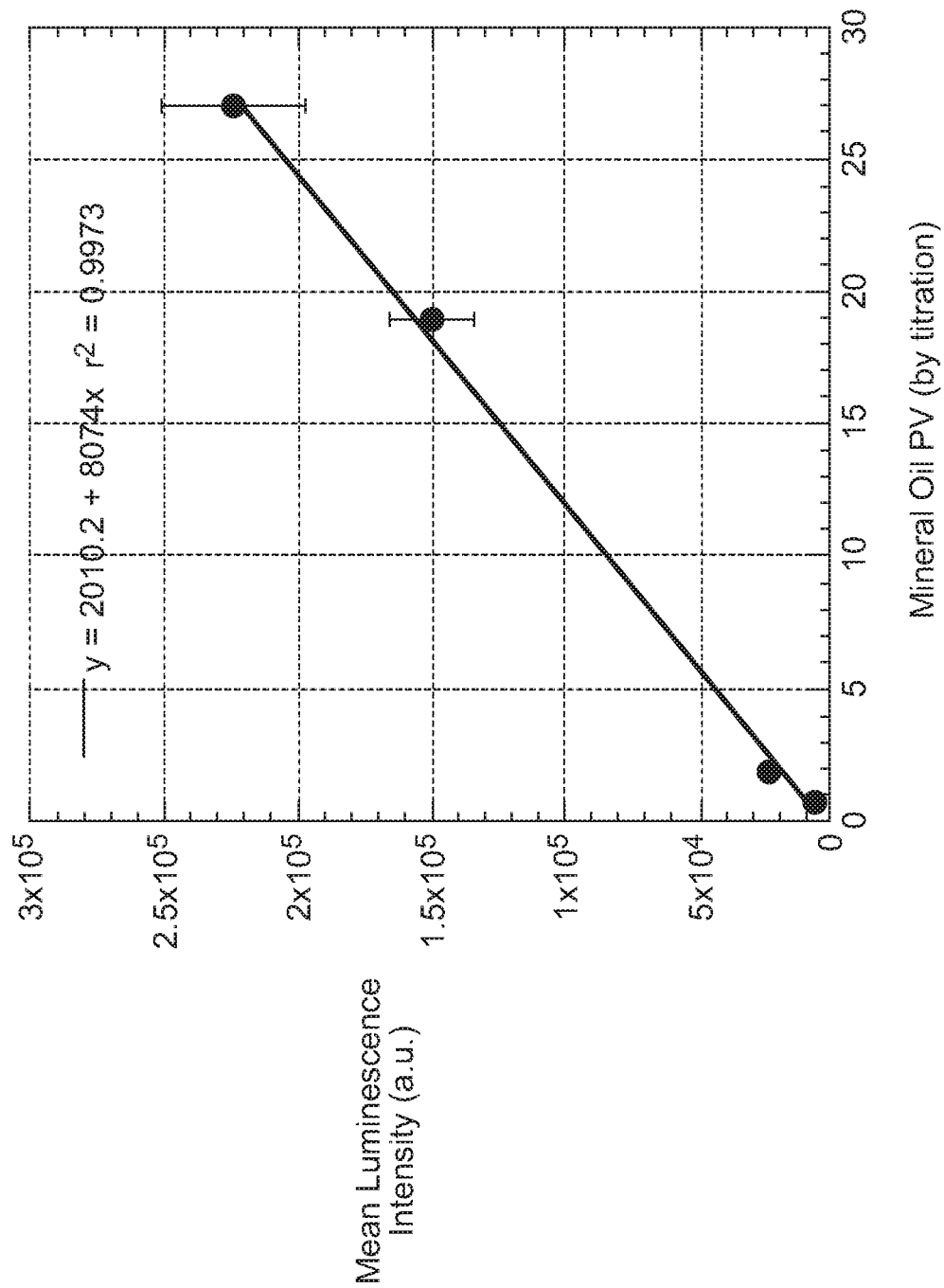

FIG. 10 illustrates mean luminescences intensity (over 12 min) from 80 mg $MnZn_4$/phytic acid in 1.5 mLs of mineral oils of various peroxide values. Peroxide values were measured by iodometric titration. Luminescence range was 350-650 nm.

Figure 11:
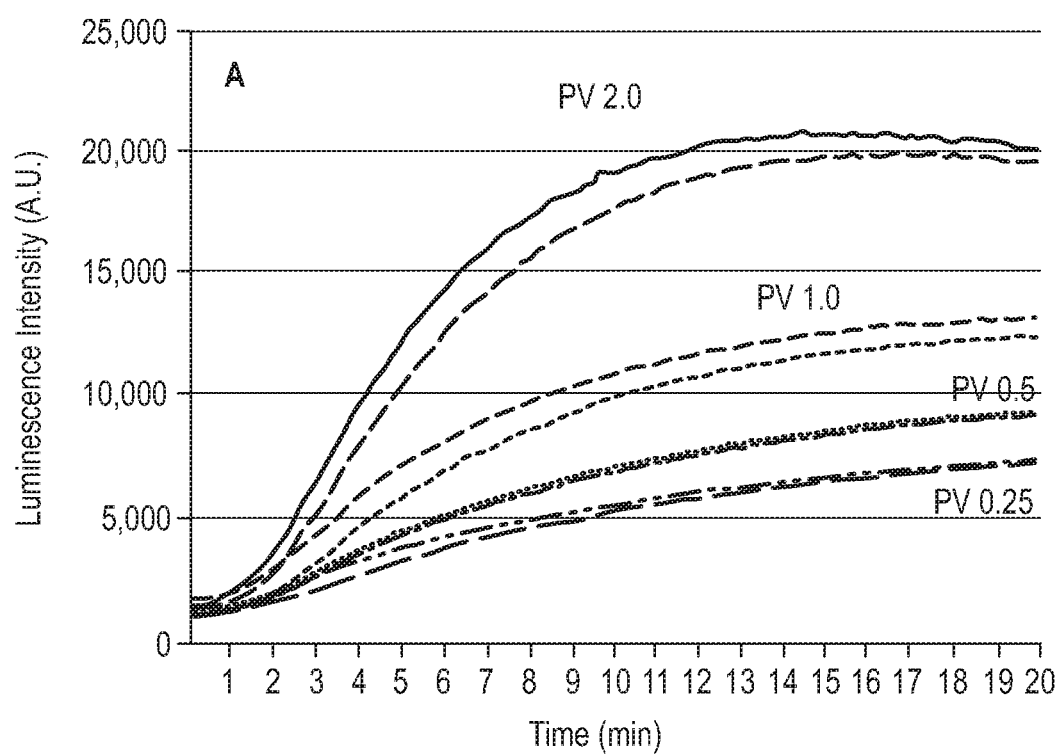

FIG. 11 illustrates luminescence emissions over time from a range of concentrations of standard cumene-hydroperoxide (CHP) in mineral oil (peroxide value 0-4.0) when mixed with 20 mg of MnZn-phytate material.

Figure 12:
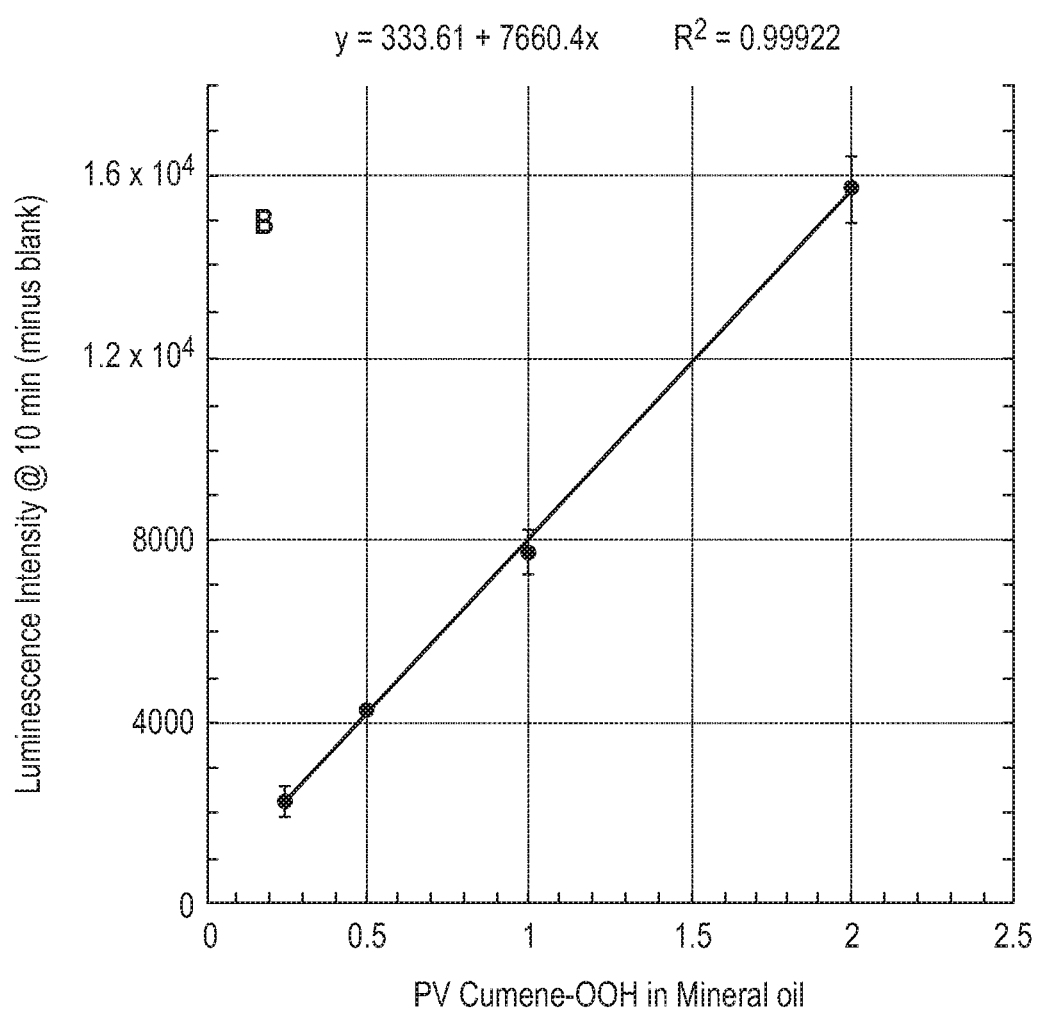

FIG. 12 illustrates a plot of the mean luminescence at each concentration at 10 minutes. Error bars show standard errors.

Figure 13:
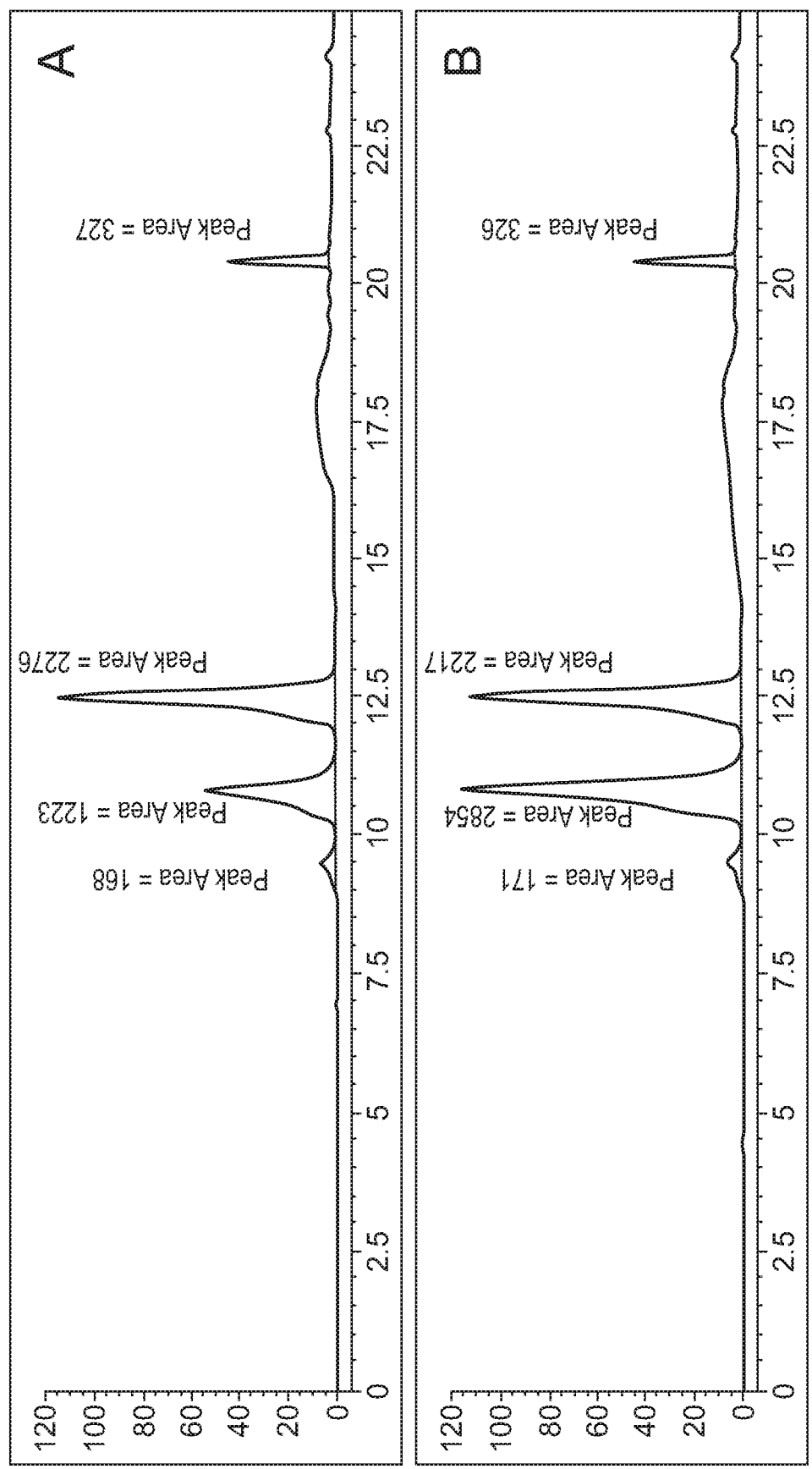

FIG. 13 illustrates reverse-phase HPLC separations of A) the control 10 mM cumene-hydroperoxide heated to 55° C. for 50 min and B) 10 mM cumene-hydroperoxide and MnZn-phytate material heated to 55° C. for 50 min. The primary peaks are 2-phenyl-2-propanol at 9.5 min, acetophenone at 10.8 min, cumene-hydroperoxide at 12.5 min and cumene at 20.4 min.

Figure 14:
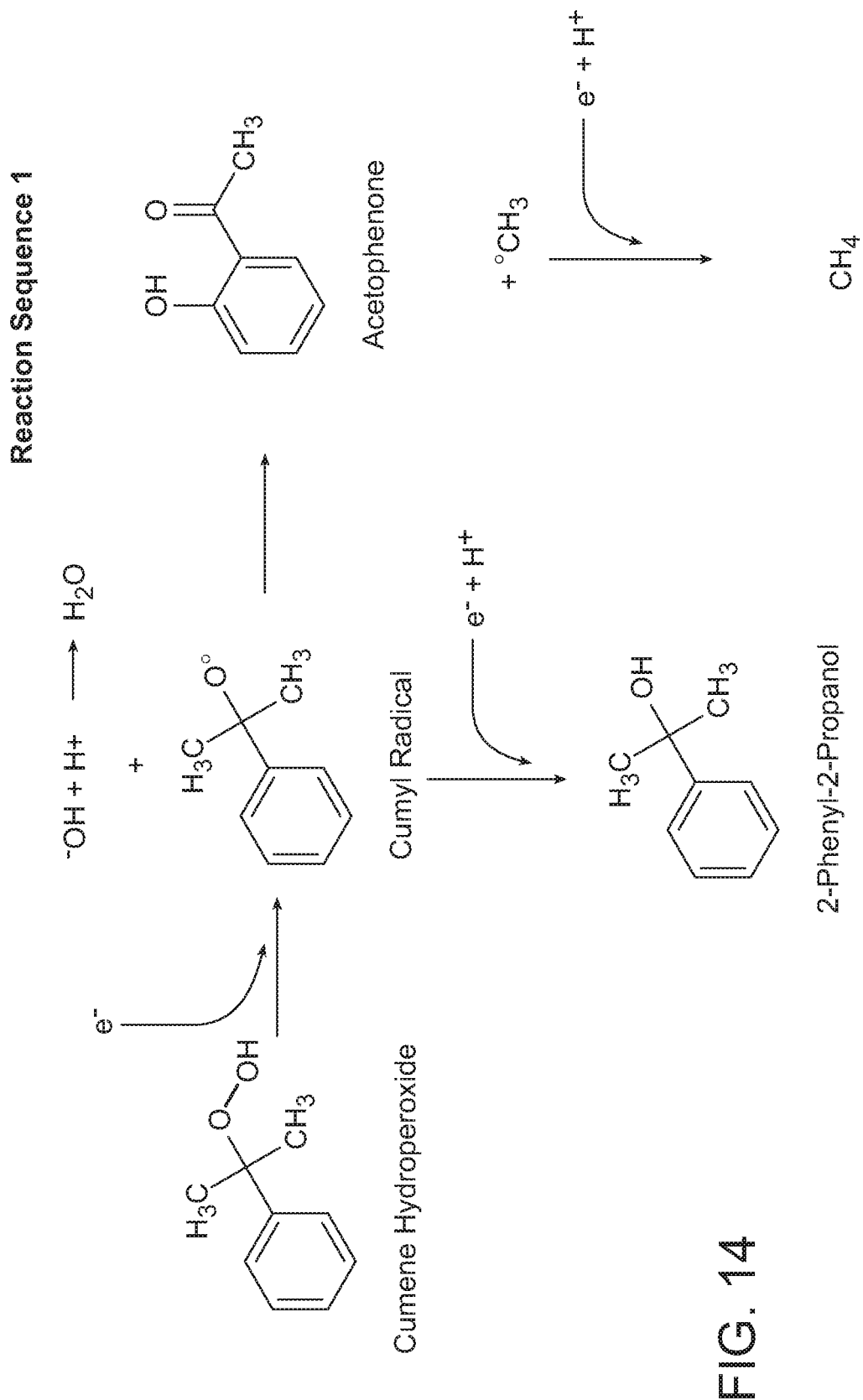

FIG. 14 illustrates degradation reaction mechanisms of cumene-hydroperoxide from one-electron reactions.

Figure 15:
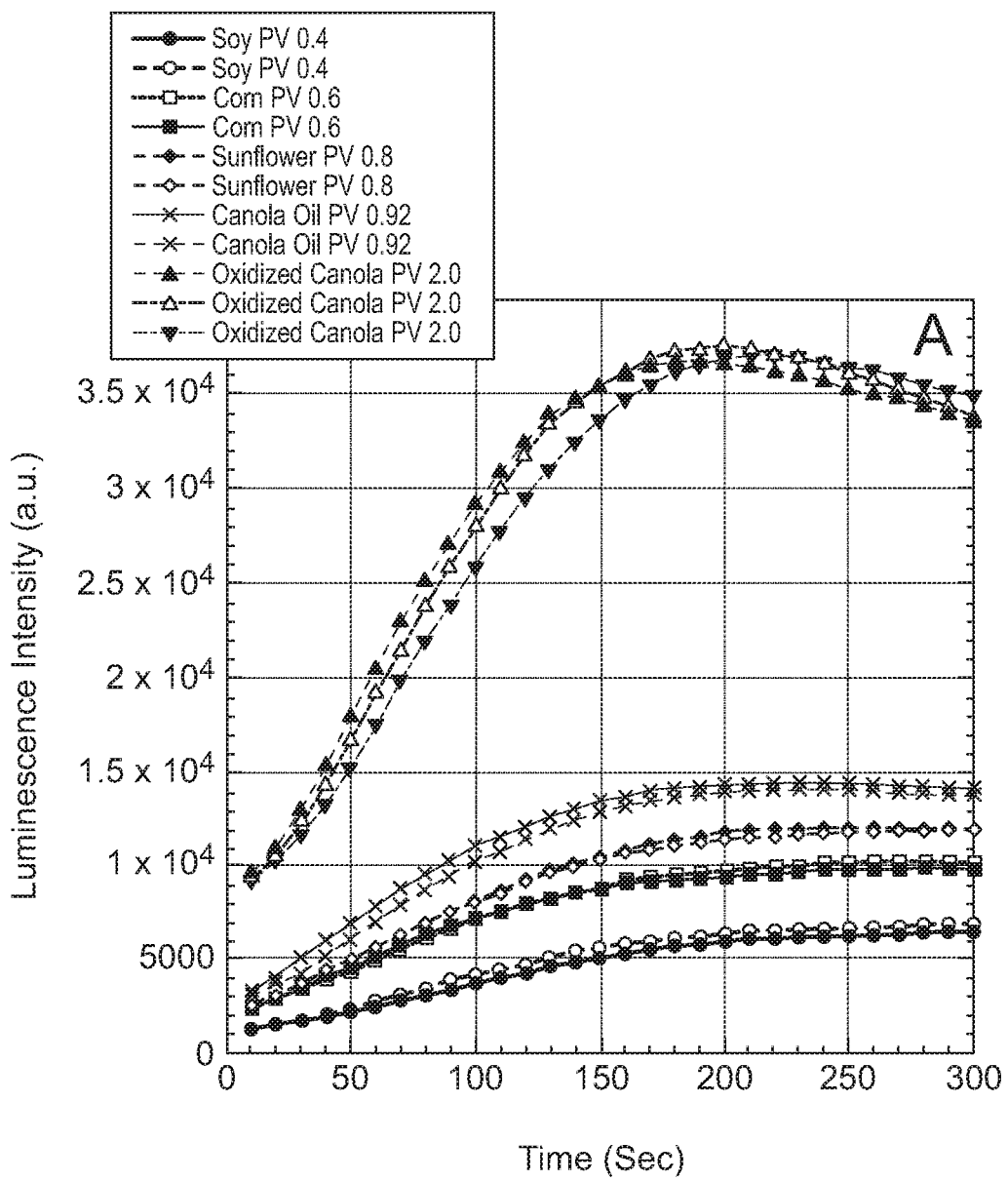

FIG. 15 shows the luminescence emissions over time from a range of concentrations of peroxide values in edible oils (peroxide value 0.4-2.0) when mixed with 20 mg of MnZn-phytate material.

Figure 16:
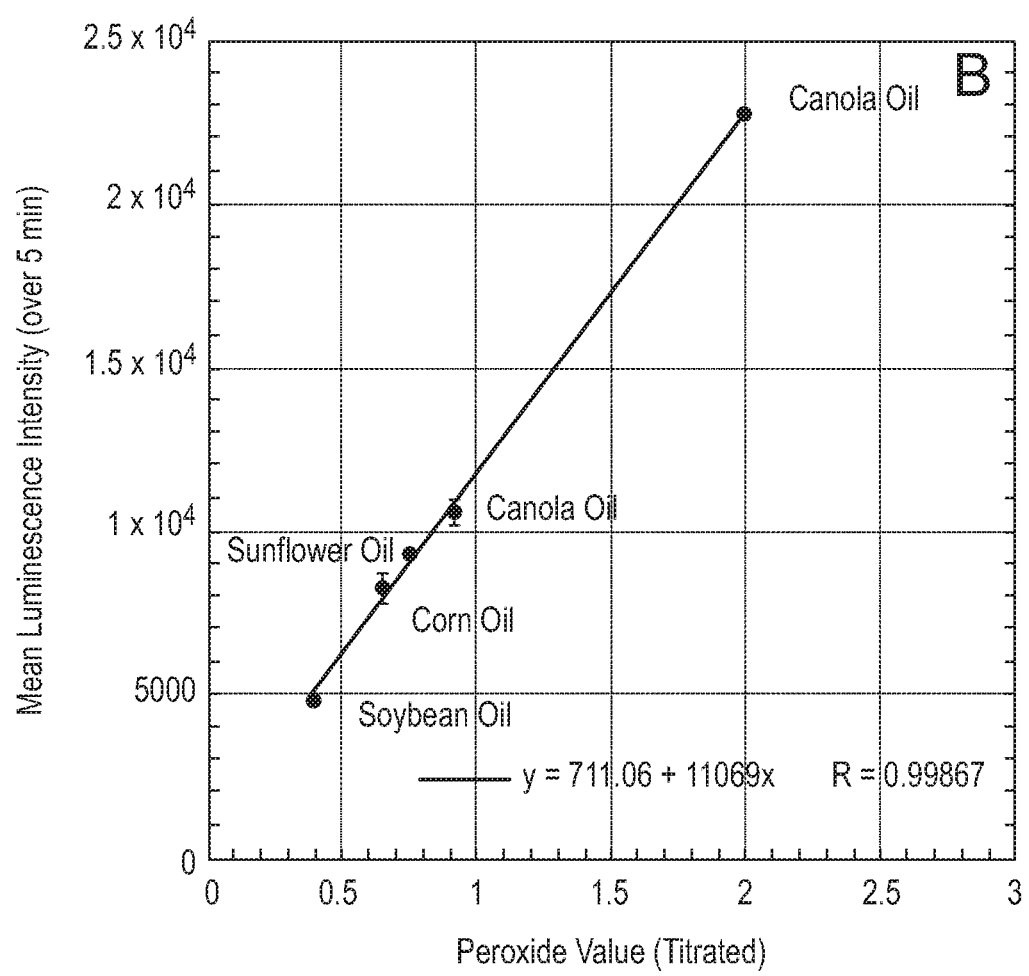

FIG. 16 shows a plot of the mean luminescence over 5 min (from data in FIG. 15) at each peroxide value in edible oils when mixed with 20 mg of MnZn-phytate material. Error bars show standard errors.

Reference will now be made in detail to the present preferred embodiments of the method and materials for performing that method, examples of which are illustrated in the accompanying drawing figures.

DETAILED DESCRIPTION

A method and structured compound semiconductor materials are provided to visualize, detect and even quantify oxidizing chemical species such as one or more free radicals (e.g. carbon, nitrogen, and oxygen radicals), one or more reactive oxygen species (ROS) or combinations thereof. This is done via the emission of electromagnetic radiation upon the transfer of an electron to, or from, the compound semiconductor materials and the oxidizing chemical species.

The electromagnetic radiation could be anywhere in the known electromagnetic spectrum, but preferably in the region of visible or infrared radiation. The amount of light emitted includes any level that could be distinguished from a reagent blank using a luminometer, fluorescence meter, spectrophotometer or other photon measuring device.

A method of monitoring for the presence of a hydroperoxide in an environment broadly includes the steps of: (a) exposing a structured compound semiconductor material with peroxidase activity to the hydroperoxide in the environment and (b) detecting electromagnetic radiation emitted by the compound semiconductor material with peroxidase activity upon exposure to the hydroperoxide. The environment may be an aqueous environment or a non-polar environment. Advantageously, the method allows for visualization, detection and quantification of organic radicals and/or ROS such as hydroperoxides in real time.

The structured compound semiconductor material with peroxidase activity may comprise and may be produced from an organic scaffold material and, more particularly a phytate scaffold material, a primary semiconducting material and a metal dopant wherein the structured compound semiconductor material with peroxidase activity emits electromagnetic radiation upon exposure to the oxidizing species. In one particularly useful embodiment, the primary semiconducting material is zinc and the metal dopant is manganese.

More specifically, the structured compound semiconductor material with peroxidase activity may comprise between about 3.0-50.0 mole percent phytate scaffold material, between about 18.0-80.0 mole percent zinc and between about 0.1 and 10.0 mole percent manganese. In other embodiments, the structured compound semiconductor material with peroxidase activity comprises more than 5.0 mole percent manganese. In one particularly useful embodiment, the structured compound semiconductor material with peroxidase activity comprises 0.1-5.0 and, more particularly, about 0.5 mole percent manganese.

The structured semiconductor material on a phytate scaffold material may be obtained from (a) organic substances, such as rice, corn, wheat, barley or soybean, either in raw or processed form, or (b) synthesized in the laboratory. The structured semiconductor material may, for example, be derived from rice bran plasma ash. In other embodiments, the structured semiconductor material may be derived synthetically from phytic acid (with or without added ethanolamine). The environment of the method may be an aqueous environment or a non-polar environment.

The method may also include the step of measuring the electromagnetic radiation emitted by the structured compound semiconductor material with peroxidase activity with any appropriate means for this purpose, such as, but not necessarily limited to a luminometer, a fluorescence meter, a spectrophotometer or other photon measuring device. The method may also include the step of quantifying the hydroperoxide in the environment by means of the measured electromagnetic radiation that is emitted.

The method may be used in the monitoring of the presence of hydroperoxide in a selected aqueous environment. The method may be used in the monitoring of the presence of hydroperoxide in a selected non-polar environment. The method may be used in the monitoring of the presence of hydroperoxide in a selected food. The method may be used in the monitoring of the presence of hydroperoxide in a selected pharmaceutical. The method may be used in the monitoring of the presence of hydroperoxide in a selected biological material. The method may be used in the monitoring of the presence of hydroperoxide in a selected petrochemical environment.

Reference is now made to the following examples that further illustrate the structured compound semiconductor and the method of monitoring for the presence of a hydroperoxide in an environment of interest.

EXAMPLE 1

Agricultural products can be used as a source of compound semiconductor materials that emit luminescence upon exposure to peroxides. More specifically, agricultural products that contain, or did contain, phytic acid (or phytate).

Inorganic crystalline components from rice protein concentrate and rice bran was ashed using two different techniques. High-temperature ashing was conducted at 550-580° C. for 24 hours utilizing an Isotemp Muffle Furnace (Thermo Fisher Scientific Inc., Pittsburgh, Pa.). Ceramic crucibles were acid washed with 6N HCl and dried to constant weight prior to analysis. Low temperature plasma ashing was achieved utilizing oxygen plasma conditions with a plasma ashing system M4L PVA (TePla America Inc., Corona, Calif.). Samples were processed in cycles of 2 hours with the equipment set at 450 W until complete removal of the organic matter, which was monitored gravimetrically to constant weight. The temperature during processing did not exceed 150° C.

Figure 1:
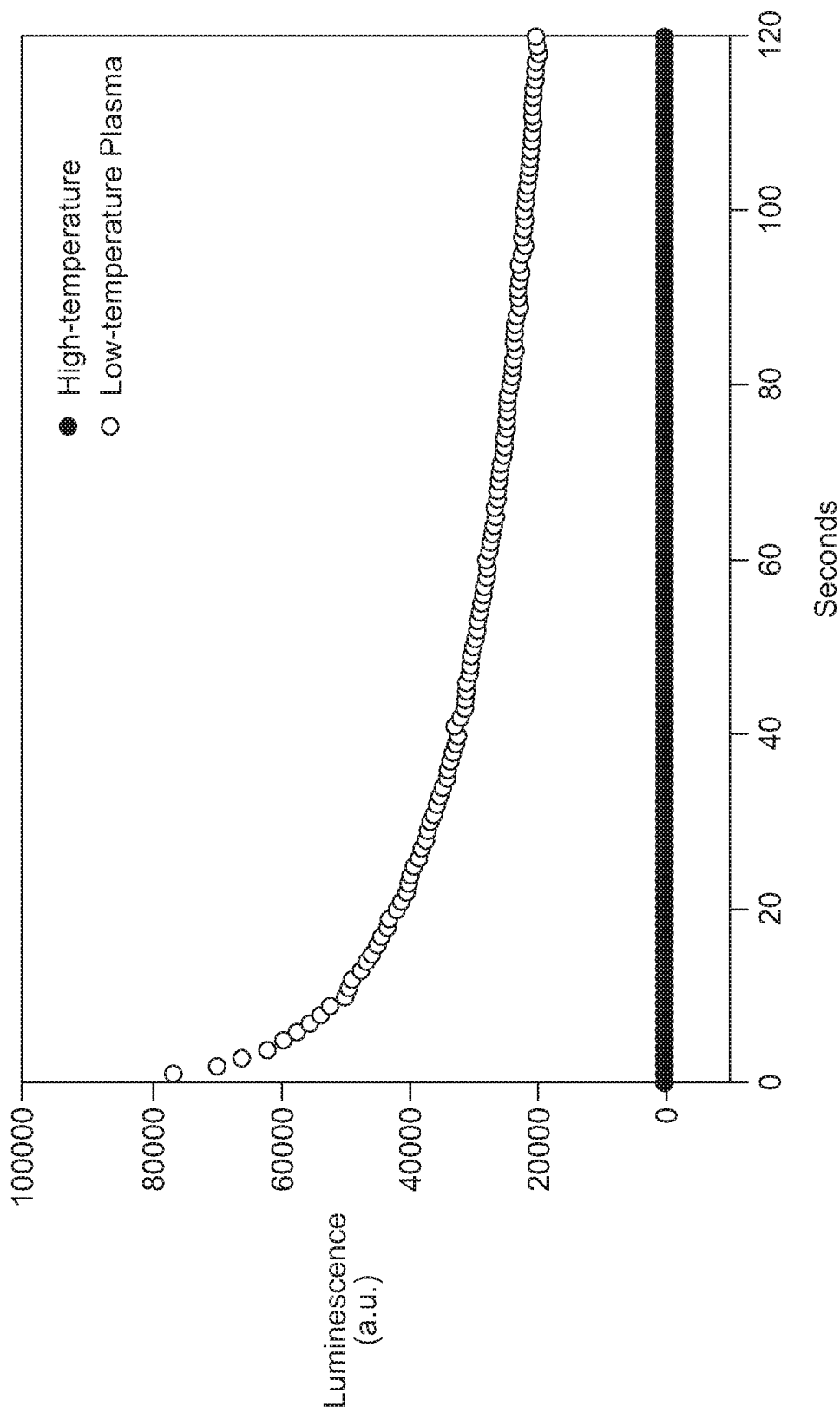

The total amount of ash obtained from the rice protein sample using the two ashing techniques revealed no statistically significant difference. FIG. 1 shows the levels of luminescence generated from these materials upon exposure to 22 mM hydrogen peroxide at pH 7.2. The sample ashed with low temperature plasma processing exhibited a burst of chemical luminescence, while the sample that was ashed at high temperature did not exhibit any significant luminescence. These findings suggest that the low temperature process maintains the native crystal structure, and this structural characteristic is required for emitting luminescence when exposed to peroxides.

Figure 2A:
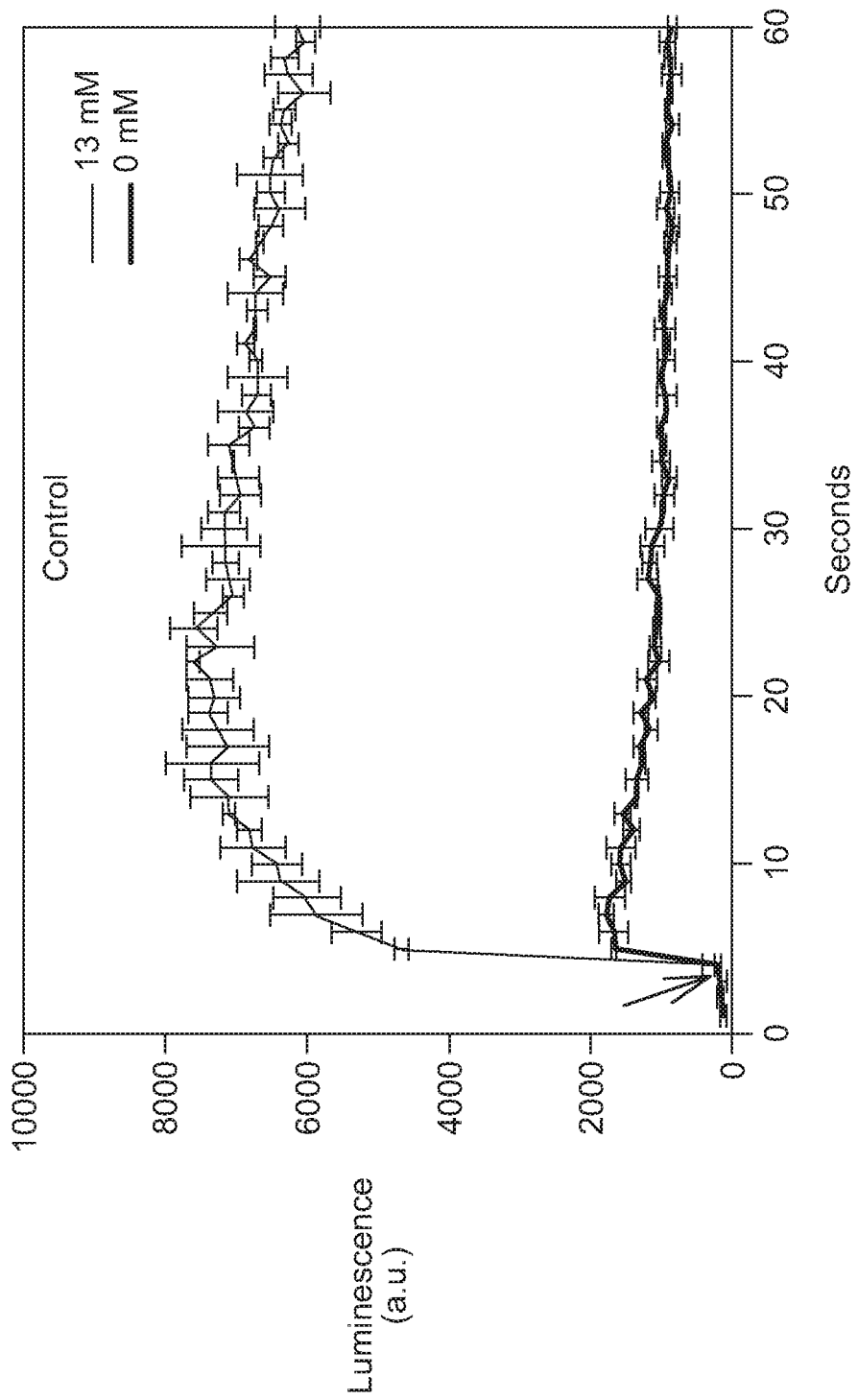
FIG. 2a illustrates the chemical luminescence emitted from non-ashed rice bran.

A similar comparison was made with rice bran ashed using the high temperature and low temperature plasma ashing techniques. FIG. 2a exhibits the chemical luminescence emitted from the non-ashed rice bran compared to the same material that had been processed with high temperature (FIG. 2b) and low temperature (FIG. 2c) ashing techniques. Comparing the same conditions of amount of sample, pH and hydrogen peroxide concentration the non-ashed sample exhibited a peak luminescence intensity of about 10,000. The plasma ashed material (representing 11.14 percent of the original rice bran) exhibited a peak luminescence intensity of 1,000,000, while the high temperature ashed material did not exhibit any significant luminescence. Again, this indicates that the low temperature process maintains the native crystal structure, and this structural characteristic is required for emitting luminescence when exposed to ROS.

EXAMPLE 2

Preparation of Compound Semiconductor Materials Using Phytic Acid as an Organic Scaffold Because rice is a known rich source of phytic acid capable of forming complexes with mono and polyvalent metals, different Mn-doped Zn phytate complexes were synthesized. Three organic-metallic frameworks containing different mole percent Mn were individually prepared, namely 0.1, 0.5, and 5.0 mole %. Briefly, 3.5 g of phytate was dissolved in 560 mL of 50% methanol followed by the addition of 16.8 mmoles of zinc sulfate heptahydrate and either 20, 85, or 850 μmoles of manganese perchlorate hexahydrate to attain 0.1, 0.5, and 5.0 mole %, respectively. Then, 2.8 mL of triethylamine was added and the solution was held at 60° C. under agitation for 3 hours; the pH was held between 7.0 and 7.2 through the addition of 0.1 N NaOH. Finally, the solution was centrifuged at 1000×g for 10 min, the precipitate was dried at 60° C. under atmosphere for 72 hours, and ground in a mortar and pestle to a fine powder.

Chemically-stimulated luminescence generated when these synthesized zinc, manganese, or zinc-manganese compounds on a phytate skeleton were exposed to hydrogen peroxide are shown in FIG. 3. Materials containing only zinc or only manganese did not generate significant luminescence. However, the combination of 0.5 mole percent manganese and zinc on the phytic acid scaffold did produce a significant amount of chemically stimulated luminescence.

EXAMPLE 3

Preparation of Compound Semiconductor Materials Using Phytic Acid-Ethanolamine as an Organic Scaffold Variations of the organic scaffold used to deposit the compound semiconductors affected the solubility of the resulting material as well as the efficiency of luminescence production. The water insoluble phytate-zinc/manganese material (discussed below) worked well for edible oils and cumene-ROOH in organic solvent. Other compositions that worked well in aqueous mediums (e.g., the plasma ash from rice bran) did not work well in non-polar mediums. Also, chemically modifying the organic scaffold by attaching ethanolamine to phytic acid before depositing the zinc and manganese strongly increased the luminescence efficiency in an aqueous environment (FIG. 4).

Effect of water soluble free radical quenchers on chemically-stimulated luminescence. Water soluble organic radical quenchers (TEMPOL, TEMPO, and POBN) were utilized to investigate the contribution of free radicals to the observed luminescent phenomena (FIG. 5). All organic radical quenchers decreased (P<0.05) the chemically-stimulated luminescence from structured compound semiconductor hydrated with hydrogen peroxide. The decrease in luminescence was as high as 94% (TEMPOL and TEMPO), demonstrating a free radical mechanism responsible for the excitation of the novel compound semiconductor material in an aqueous environment.

The light emission from an excited state of Mn (II) is typically associated with the $^4T_1 \rightarrow ^6A_1$ transition with a characteristic wavelength of around 500-600 nm (Gumlich, 1981). In order to investigate the wavelength distribution of the light emitted from the chemically-stimulated luminescence from structured compound semiconductors, optical band-pass filters (Omega Optical, Brattleboro, Vt.) were utilized. The range of 500-550 nm was the major contributor to the chemically-stimulated luminescence in aqueous samples (FIG. 6) further suggesting the involvement of excited state of Mn (II). Furthermore, light emission at wavelengths>650 nm represented only 3% of the total luminescence. This indicates that the contribution of excited state singlet oxygen, with light emission around 630, 700, and 1260 nm (Khan & Kasha, 1966; Khan, 1989; Schweitzer & Schmidt, 2003), could be no more than a minor component of the observed chemically-stimulated luminescence.

Examination of the potential contribution of singlet oxygen to the chemically-stimulated luminescence. The effect of the singlet oxygen quencher, azide anion, was examined. When the control material (shown in FIG. 5) was treated with 12.5 mM sodium azide, greater than 90 percent of the luminescence intensity remained. This further demonstrates that singlet oxygen is not a major contributor.

Requirement of specific organic scaffolding. For comparison a Mn-doped ZnS nanoparticle material was synthesized according to the procedure of Zhuang and others (2003). The material exhibited photo-luminescence characteristics, and contained a composition of semiconductors similar to the functional material described in the current proposal. However, it did not emit luminescence when chemically stimulated with hydrogen peroxide. This observation further indicates that the phytate-specific scaffolding is a key feature necessary for the chemically-stimulated luminescence from the structured compound semiconductors hydrated with peroxides.

Figure 2B:
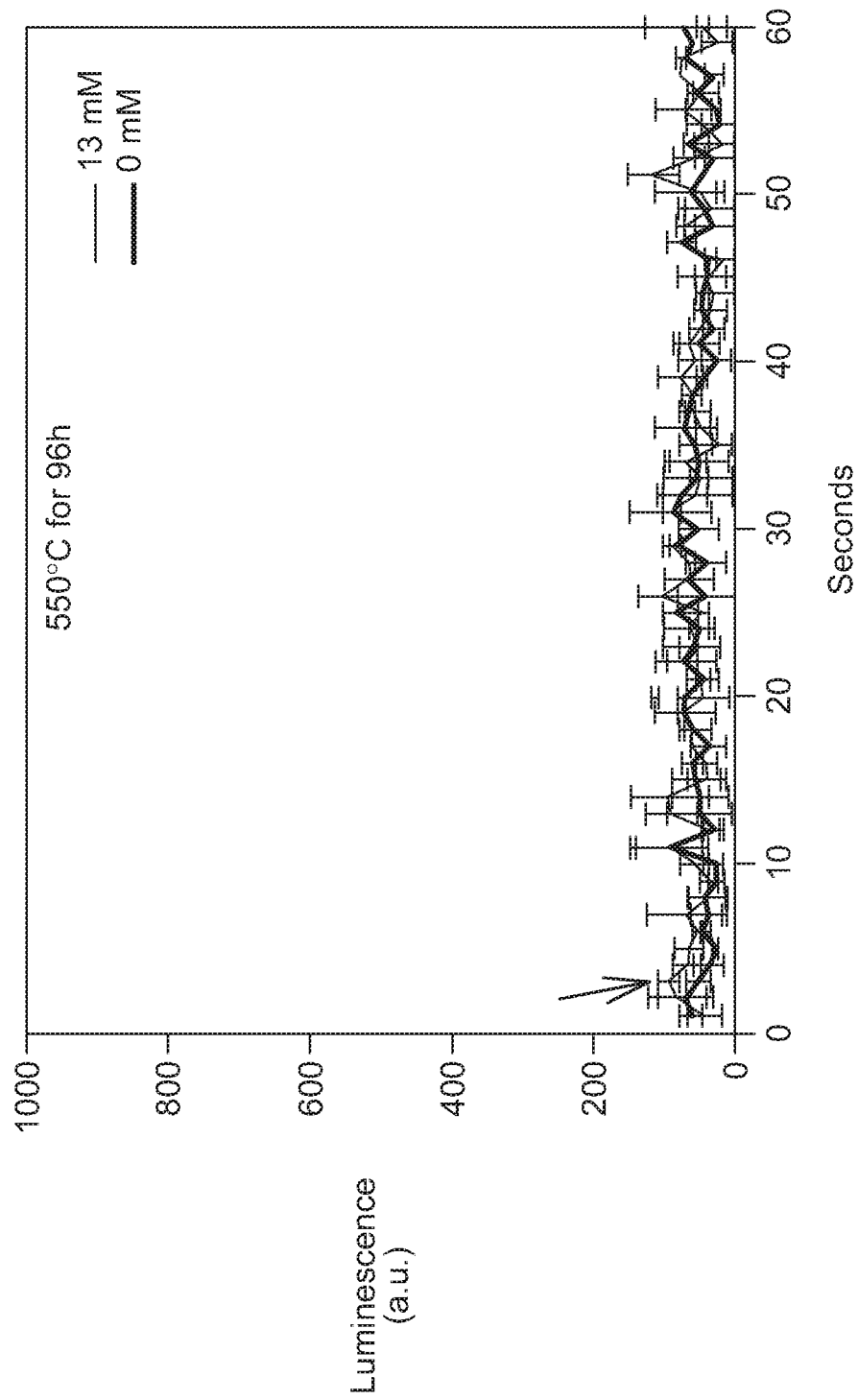
FIG. 2b illustrates the chemical luminescence emitted from rice bran ashed at high temperature (580° C.).
Figure 2C:
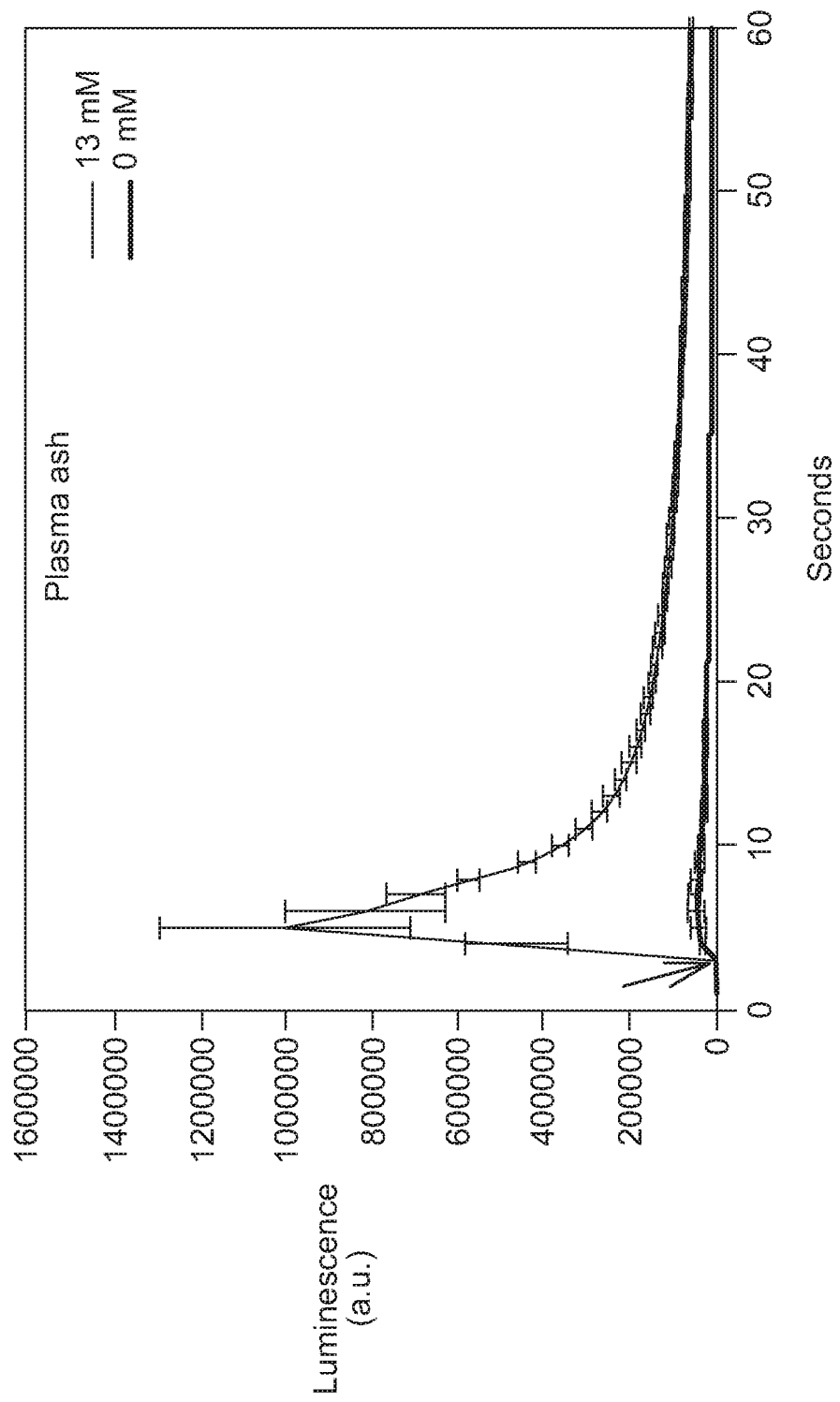
FIG. 2c illustrates the chemical luminescence emitted from rice bran plasma ashed at low temperature (150° C.).

Thermally-induced disturbance of the structured lattice. In order to investigate the influence of the organized structure of the synthesized compound on the chemically stimulated luminescence, a high-temperature ashing process (muffle furnace at 550° C. for 96 h) was utilized to disrupt the framework of this material (FIG. 2b). The same material ashed using a low-temperature ashing technique (oxygen plasma) did not negatively affect the chemically-stimulated luminescence from naturally occurring phytate-rich powders (FIG. 2c). The high-temperature ashing eliminated the luminescence from zinc manganese structured compound semiconductors materials when exposed to hydrogen peroxide. These observations indicate that the novel material exhibits the luminescent phenomena based not only on its chemical composition, but the underlying organized structure as well.

EXAMPLE 4

Use of Compound Semiconductor on a Phytate Scaffold to Measure Peroxide Value (PV) in Edible Oil An advantage of the zinc/manganese material deposited on the phytate scaffold (without added ethanolamine) is the generation of luminescence in a non-polar environment, such as edible oil (FIG. 8). The intensity of luminescence shows a strong correlation with the peroxide value of the oil (FIG. 9).

EXAMPLE 5

Use of Compound Semiconductor on a Phytate Scaffold to Measure Peroxide Value (PV) in Mineral Oil The petrochemical industry is another common field that requires the measurement of hydroperoxides as peroxide values (PV) in products that include mineral oils, transformer oils and jet fuels. As in the edible oil industry, an iodometric titration is typically used (e.g., ASTM D3703-99). Similar to data obtained from vegetable oils (FIG. 8), the intensity of luminescence from mineral oil shows a strong correlation with the peroxide value (FIG. 10).

Materials and Methods

Materials. Hydrogen peroxide (cat. BDH7690-1), methanol (cat. BDH20864), and triethylamine (cat. 89500-556) was purchased from VWR international Ltd., and sodium azide (cat. S8032), 2,2,6,6-tetramethylpiperidinyloxy (TEMPO; cat. 21400), and phytic acid sodium salt hydrate (cat. P8810, mole ratio of Na to phytate at 5:1) from Sigma-Aldrich. Zinc sulfate heptahydrate (cat. 33399), ethanolamine (cat. 36260) was supplied by Alfa Aesar and manganese (II) perchlorate hexahydrate (cat. 316511000) and inositol hexaphosphoric acid 50% aqueous solution (cat. 235370010) was provided by ACROS Organics. α-(4-Pyridyl 1-oxide)-N-tert-butylnitrone (POBN, cat. ALX-430-091) and 4-Hydroxy-2,2,6,6-tetramethylpiperidinyloxy (TEMPOL; cat. ALX-430-081) was purchased from Enzo Life Sciences. All aqueous solutions were prepared using a NANOpure Diamond water purification system operating at 18.2 MΩcm of resistivity.

Synthesis of structured compound semiconductors, Example 1. Briefly, 3.5 g of phytic acid was solubilized in 50 mL of nanopure water followed by the addition of ligands if applicable (e.g., 250 μL of ethanolamine). The solution was held at certain temperature (e.g., 30 degrees C.) for 1 hour under vacuum (20,000 mTorr) followed by an additional period (180 min) under higher vacuum (10–5 mTorr). The dried product was dissolved in 400 mL of water-methanol solution followed by the addition of 16.8 mmoles of zinc sulfate heptahydrate and different mole percent levels of manganese perchlorate hexahydrate. Then, a volume of triethylamine (e.g., 0.5 v/v %) was added and the solution was warmed (e.g., 65 degrees C.) in a water bath under agitation; the pH was held between 7.0 and 7.2 by adding 0.1 N NaOH. Finally, about half of the solvent volume was removed under vacuum at 60° C. for 3 hours, and the precipitate was freeze-dried.

As further illustrated with reference to FIGS. 11-14, the structured compound semiconductor material has been shown to possess peroxidase activity thereby making it useful in a method of monitoring for the presence of a hydroperoxide in an environment. More particularly, the structured compound semiconductor material has the ability to emit luminescence proportional to the content of peroxides in various types of materials.

A primary one-electron mechanism for the peroxidase-like reaction forming acetophenone from a cumene-hydroperoxide (CHP) standard has been demonstrated. See FIGS. 11-14. This reaction is responsible for the emission of luminescences proportional to the concentration of cumene-hydroperoxide (or other hydroperoxides). When using single point data obtained with cumene-hydroperoxide in mineral oil, values at 10 min were used to compare with data from edible oils at 5 min due (as shown in FIG. 16), in part, to the heat transfer coefficient difference (soybean oil 0.165 $W/m^2 \cdot K$ vs. mineral oil 0.145 $W/m^2 \cdot K$).

Reverse-phase HPLC separations of the components from the light-emitting reaction of cumene-hydroperoxide with MnZn-phytate material revealed that the primary product is acetophenone (FIG. 13). The standard cumene-hydroperoxide is about 80 percent pure and the HPLC chromatogram are obtained at 254 nm which emphasizes acetophenone and its change over time. Cumene hydroperoxide, 2-phenyl-2-propanol and cumene have minor absorption at 254 nm.

These results demonstrate that the light-emitting reaction of the MnZn-phytate material with hydroperoxides involves a peroxidase-like one electron mechanism. FIG. 14 shows this proposed reaction mechanism forming acetophenone, and other possible one-electron reactions involving cumene-hydroperoxides.

Finally, FIGS. 15 and 16 show, respectively, (a) luminescence emissions over time from a range of concentrations of peroxide values in edible oils when mixed with MnZn-phytate material and (b) mean luminescence at each concentration over 5 minutes.

The foregoing has been presented for purposes of illustration and description. It is not intended to be exhaustive or to limit the embodiments to the precise form disclosed. Obvious modifications and variations are possible in light of the above teachings. All such modifications and variations are within the scope of the appended claims when interpreted in accordance with the breadth to which they are fairly, legally and equitably entitled.

What is claimed:

1. A method of monitoring for presence of a hydroperoxide in an environment, comprising:
    exposing a structured compound semiconductor material with peroxidase activity to said hydroperoxide in said environment; and
    detecting electromagnetic radiation emitted by said structured compound semiconductor material with peroxidase activity upon exposure to said hydroperoxide,
    wherein said structured compound semiconductor material with peroxidase activity is produced from a phytate scaffold material and a metal dopant, said structured compound semiconductor material with peroxidase activity emitting electromagnetic radiation upon exposure to the hydroperoxide.

2. The method of claim 1, further including measuring said electromagnetic radiation emitted by said structured compound semiconductor material with peroxidase activity.

3. The method of claim 2, further including quantifying the hydroperoxide in said environment by means of the measured electromagnetic radiation that is emitted.

4. The method of claim 3, including monitoring the presence of the hydroperoxide in an aqueous environment.

5. The method of claim 3, including monitoring the presence of the hydroperoxide in a non-polar environment.

6. The method of claim 3, including monitoring the presence of the hydroperoxide in food.

7. The method of claim 3, including monitoring the presence of the hydroperoxide in pharmaceuticals.

8. The method of claim 3, including monitoring the presence of the hydroperoxide in biological materials.

9. The method of claim 3, including monitoring the presence of the hydroperoxide in petrochemical materials.

10. A structured compound semiconductor material with peroxidase activity, comprising: a phytate scaffold material, a primary semiconducting material and a metal dopant wherein said structured compound semiconductor material with peroxidase activity emits electromagnetic radiation upon exposure to a hydroperoxide.

11. The structured compound semiconductor material with peroxidase activity of claim 10, wherein said primary semiconducting material is zinc.

12. The structured compound semiconductor material with peroxidase activity of claim 11, wherein said metal dopant is manganese.

13. The structured compound semiconductor material with peroxidase activity of claim 12, wherein said phytate is provided at 3.0-50.0 mole percent, said zinc is provided at 18-80 mole percent and said manganese is provided at 0.1-10.0 mole percent.

14. The structured compound semiconductor material with peroxidase activity of claim 12, wherein said manganese is provided at about 0.5 mole percent.

15. The structured compound semiconductor material with peroxidase activity of claim 10, wherein said phytate scaffold material is derived from phytic acid.

16. The structured compound semiconductor material with peroxidase activity of claim 10, wherein said phytate scaffold material is derived from rice bran plasma ash or other natural source.

17. The structured compound semiconductor material with peroxidase activity of claim 10, in an aqueous environment.

18. The structured compound semiconductor material with peroxidase activity of claim 10, in a non-polar environment.

* * * * *